United States Patent [19]
Corlew

[11] Patent Number: 6,030,393
[45] Date of Patent: Feb. 29, 2000

[54] NEEDLE AND PROCEDURE FOR RELIEVING URINARY INCONTINENCE

[76] Inventor: Earvin L. Corlew, 42440 52nd St. West, Quart Hill, Calif. 93536

[21] Appl. No.: 09/153,435

[22] Filed: Sep. 15, 1998

[51] Int. Cl.[7] .................................................. A61B 17/04
[52] U.S. Cl. .......................... 606/148; 606/144; 606/147
[58] Field of Search ..................... 606/222, 144, 606/148, 139, 147, 224

[56] References Cited

U.S. PATENT DOCUMENTS

| | | | |
|---|---|---|---|
| 3,840,017 | 10/1974 | Violante | 128/340 |
| 5,112,344 | 5/1992 | Petros | 606/148 |
| 5,123,429 | 6/1992 | Schwarz | 128/885 |
| 5,123,910 | 6/1992 | McIntosh | 606/223 |
| 5,149,329 | 9/1992 | Richardson | 604/272 |
| 5,281,237 | 1/1994 | Gimpelson | 606/144 |
| 5,387,227 | 2/1995 | Grice | 606/222 |
| 5,433,722 | 7/1995 | Sharpe et al. | 606/148 |
| 5,611,515 | 3/1997 | Benderev et al. | 128/898 |
| 5,741,276 | 4/1998 | Poloyko et al. | 606/144 |
| 5,899,909 | 5/1999 | Claren et al. | 606/119 |
| 5,904,692 | 5/1999 | Steckel et al. | 606/139 |
| 5,919,199 | 7/1999 | Mers Kelly et al. | 606/139 |
| 5,928,252 | 7/1999 | Steadman et al. | 606/148 |

Primary Examiner—Michael Buiz
Assistant Examiner—Tina T. D. Pham
Attorney, Agent, or Firm—Donald J. Ersler

[57] ABSTRACT

An incontinence needle includes a needle, a finger grip, and a suture. The needle has an atraumatic tip on one end and the suture swaged on the other end thereof. The finger grip includes a rocker arm, a slidable base and a pivot pin. The slidable base contains a bore which passes through the length thereof. The rocker arm has a cam surface on the bottom thereof which prevents movement of the finger grip relative to the needle in a first position and allows sliding in a second position. The rocker arm is pivotal mounted to the slidable base. The finger grip is used to drive the needle through body tissue. The incontinence needle is used in the following manner. An incision is made in the abdomen above the public bone. The finger grip is locked at a comfortable position along the length of the needle. A forefinger and thumb of one hand are used to guide the needle through the tissue and the forefinger and thumb of the other hand is used to drive the needle into the incision and body tissue. As the needle travels through the tissue, the finger grip may be unlocked, slid back and then relocked with the driving forefinger and thumb. The guiding forefinger is used to help prevent the needle from piercing the urethra and to ensure that the needle exits above the vagina.

17 Claims, 6 Drawing Sheets

NEEDLE AND PROCEDURE FOR RELIEVING URINARY INCONTINENCE

BACKGROUND OF THE INVENTION

1. Field of the Invention

The present invention relates generally to needles and surgical procedures and more specifically to a needle and procedure for relieving urinary incontinence which does not cause trauma to tissue in the female pubic region.

2. Discussion of the Prior Art

The present method for treating female incontinence utilizes a needle having a eye needle point. The needle is first inserted above the pubic bone. The needle is then driven behind the pubic bone, around the urethra, and out of the body, above the vagina. A suture is placed in the eye needle point and the needle is pulled back through the original needle path. This procedure can cause trauma and damage to the tissue surrounding the needle path. Further, the sharp point of the needle may pierce the surgeon's glove, because the surgeon must guide the needle when it exits the body above the vagina. A pierced glove will result in an injured finger and possible exposure to diseases such as AIDS.

U.S. Pat. No. 5,112,344 to Petros addresses the issue of trauma when the needle is pulled back through the tissue path by utilizing a protective tube to bring the suture through the needle path. However, the Petros device has a sharp tip and the protective tube must be pulled out. The sharp point may pierce the surgeon's glove during or after the operation, thus injuring the finger or exposing the surgeon to diseases such as AIDS. The diameter of the protective tube must be larger than the needle and must be withdrawn which may cause trauma and damage to tissue along the insertion path.

Accordingly, there is a clearly felt need in the art for a needle and procedure for relieving urinary incontinence which does not cause trauma or damage to tissue.

SUMMARY OF THE INVENTION

The primary objective of the present invention is to provide a needle and procedure for relieving urinary incontinence which does not cause trauma or damage to tissue.

According to the present invention, an incontinence needle includes a needle, a finger grip, and a suture. The needle has an atraumatic or blunt tip on one end and the suture swaged on the other end thereof. The needle is preferably flexible to allow bending thereof after insertion. The finger grip includes a rocker arm, a slidable base and a pivot pin. The slidable base contains a bore which passes through the length thereof. The bore is shaped to be slidable with the cross-section of the needle. The rocker arm has a finger grip surface on the top and a cam surface on the bottom thereof. A cavity is formed in the top of the slidable base to receive the rocker arm. A portion of the cavity breaks through to the bore. The rocker arm is pivotally mounted to the slidable base by driving the pivot pin through rocker arm and slidable base. In a first position, the cam surface prevents movement of the finger grip relative to the needle, in the second position, the finger grip may be slid on and off the needle. The finger grip is used to drive the needle through tissue.

The incontinence needle is used in the following manner. An incision is made in the abdomen preferably 2–3 inches above the pubic bone. The atraumatic tip is inserted into the incision. The finger grip is locked at a comfortable position along the length of the needle. A forefinger and thumb of one hand is used to guide the needle through the tissue and the forefinger and thumb of the other hand is used to drive the needle. As the needle travels through the tissue, the finger grip is unlocked, slid back and then relocked with the driving forefinger and thumb. The needle will pass behind the pubic bone and then around the urethra. The needle must not nick or pierce the urethra. The guiding forefinger is used to ensure that the needle exits above the vagina. Once the needle fully exits the body, the suture is cut off the end and each end of the suture is tied or attached together. Two sutures are required, one on the left side of the urethra and the other on the right side of the urethra.

Accordingly, it is an object of the present invention to provide an incontinence needle which has a blunt tip which will not induce trauma or damage to tissue.

It is a further object of the present invention to provide an incontinence needle which does not have to be pulled through tissue a second time.

It is yet a further object of the present invention to provide an incontinence needle which has a tip which will not injure or expose a surgeon to the risk of a fatal disease.

Finally, it is another object of the present invention to provide a pereyra needle which does not create a bigger cavity than needed.

These and additional objects, advantages, features and benefits of the present invention will become apparent from the following specification.

BRIEF DESCRIPTION OF THE DRAWINGS

FIG. 1a is a perspective view of a finger grip with a cross cavity for retaining a thumb in accordance with the present invention;

DETAILED DESCRIPTION OF THE PREFERRED EMBODIMENTS

Figure 1:
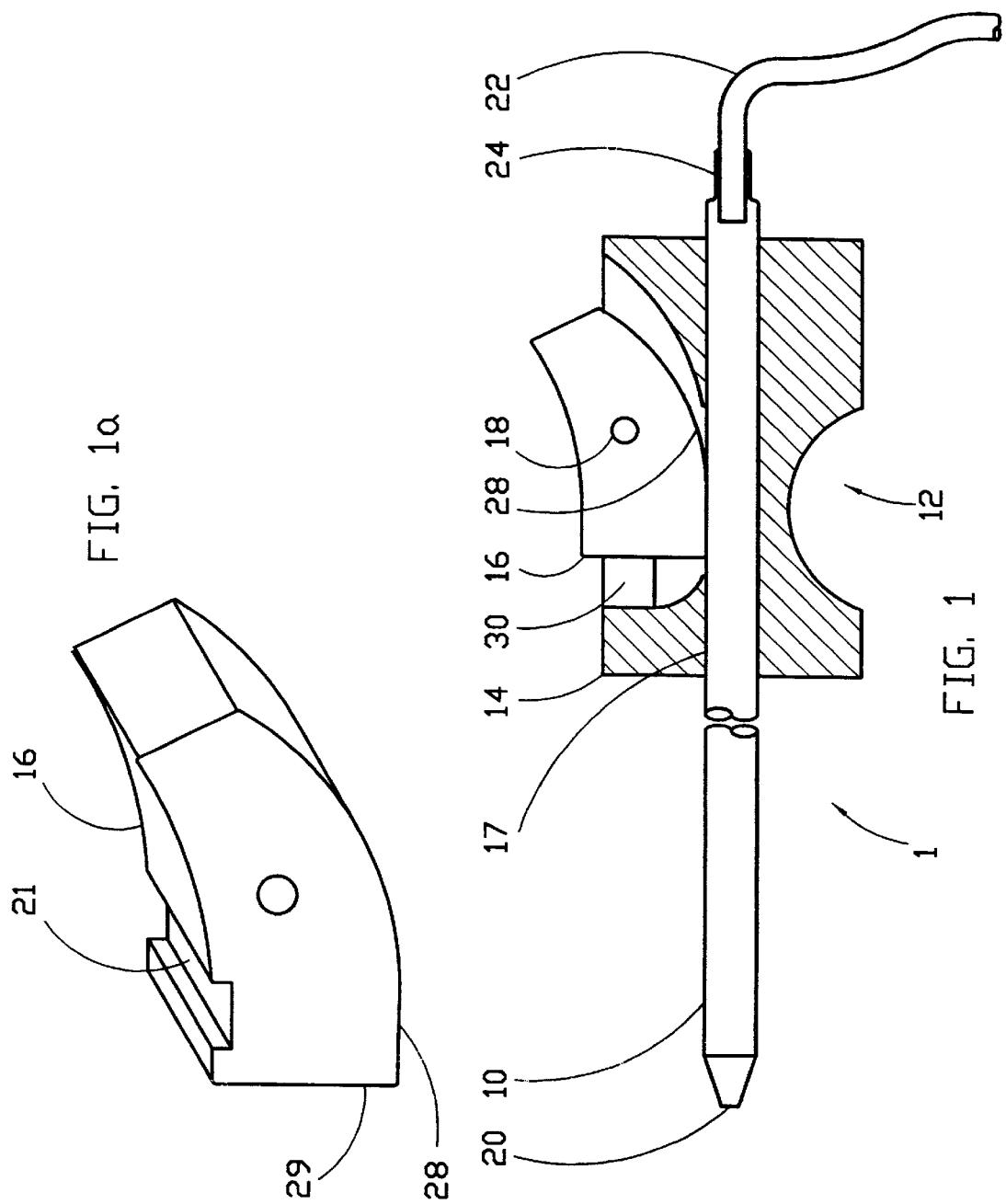
FIG. 1 is a cross-sectional view of a finger grip and a needle in accordance with the present invention.
Figure 2:
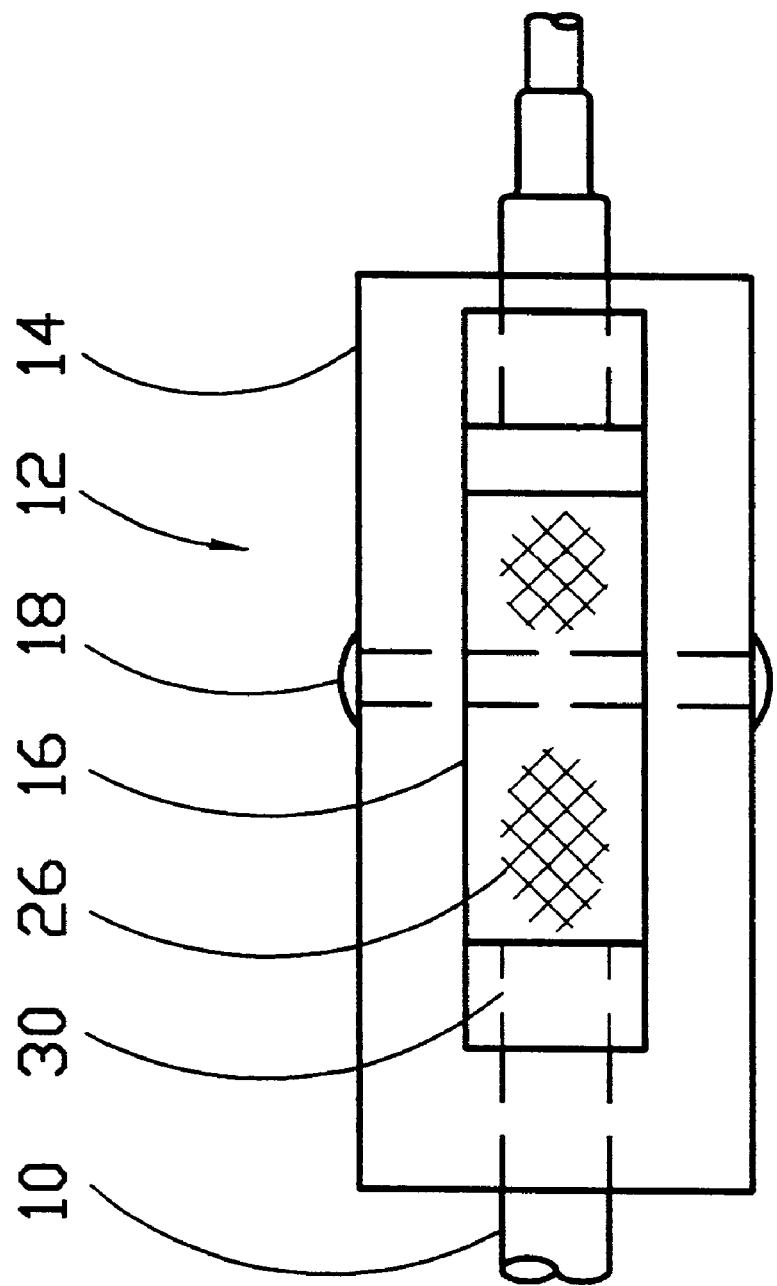
FIG. 2 is a top view of a finger grip and a needle in accordance with the present invention.
Figure 3C:
FIG. 3c is a side view of a second atraumatic tip of an incontinence needle in accordance with the present invention.
Figure 3D:
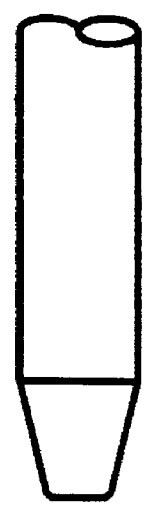
FIG. 3d is a side view of a third atraumatic tip of an incontinence needle in accordance with the present invention.

With reference now to the drawings, and particularly to FIG. 1, there is shown an incontinence needle 1. The incontinence needle 1 includes a needle 10, a finger grip 12, and a suture 22. With reference to FIGS. 2–3d, the needle 10 has an atraumatic or blunt tip 20 on one end and a suture 22 which is internally swaged on the other end thereof. The outside perimeter 24 of the swaged area is less than the perimeter of the cross section of the needle 10. The needle 10 is preferably flexible to allow bending before and after insertion into body tissue. The cross sectional shape of the needle 10 is preferably round, but could be square, oval, trapezoidal, triangular, or an other suitable shape.

The finger grip 12 includes a rocker arm 16, a slidable base 14 and a pivot pin 18. The slidable base 14 contains a bore 17 which passes through the length thereof. The bore 17 is sized to be slidable with the cross section of the needle 10. The rocker arm 16 has a non-slip surface 26 on the top and a cam surface 28 on the bottom thereof. Preferably, the lobe of the cam surface 28 increases as the cam surface 28 approaches a first end 29, such that as a thumb is pressed down in a first position, it becomes increasingly difficult to move the finger grip 12 relative to the needle 10. The non-slip surface 26 is treated such that a thumb will not move relative to the rocker arm 16. The non-slip surface 26 may be implemented by knurling, roughening, small cross projections, or any other method which does not allow a thumb to move relative to the non-slip surface 26. With reference to FIG. 1a, a cross cavity 21 may be formed on the rocker arm 16 to ensure that a thumb does not slip off thereof. The bottom of the cross cavity 21 may also be made into a non-slip surface 26.

A cavity 30 is formed in the top of the slidable base 14 to receive the rocker arm 16. A portion of the cavity 30 breaks through the bore 17. The rocker arm 16 is pivotal mounted to the slidable base 14 by driving the pivot pin 18 through rocker arm and slidable base 12. The pivot pin 18 may be retained by swaging the ends thereof. FIG. 1 shows the rocker arm 16 in the first position or driving position. When the rocker arm 16 is in the first position, the cam surface 28 prevents movement of the finger grip 12 relative to the needle. When the rocker arm 16 is rotated to the second position, the finger grip 12 may be slid along the length of the needle 10. The finger grip 12 is used to drive the needle 10 through body tissue. A cutout 31 may be formed in a bottom of the slidable base 14. The cutout 31 allows a forefinger to be inserted therein to help prevent slippage between the forefinger and the slidable base 14.

Figure 3A:
FIG. 3a is a side view of a square tip of an incontinence needle in accordance with the present invention.
Figure 3B:
FIG. 3b is a side view of a first atraumatic tip of an incontinence needle in accordance with the present invention.

The following dimensions are given by way of example and not by way of limitation. It is preferable that the length of the needle be 10 inches long. It is preferable that the length of the suture be 27 inches long. If the needle has a round cross section, it is preferable that the diameter be between 0.032–0.080 inches. FIGS. 3a–3d show some of the shapes which may be used for the blunt tip 20. It is preferable that the atraumatic tip be as shown in FIG. 3a, but the shape of tips shown in FIGS. 3b–3d would also work satisfactorily. The shape of blunt tip 20 should not be limited to only those shown in FIGS. 3a–3d.

Figure 4:
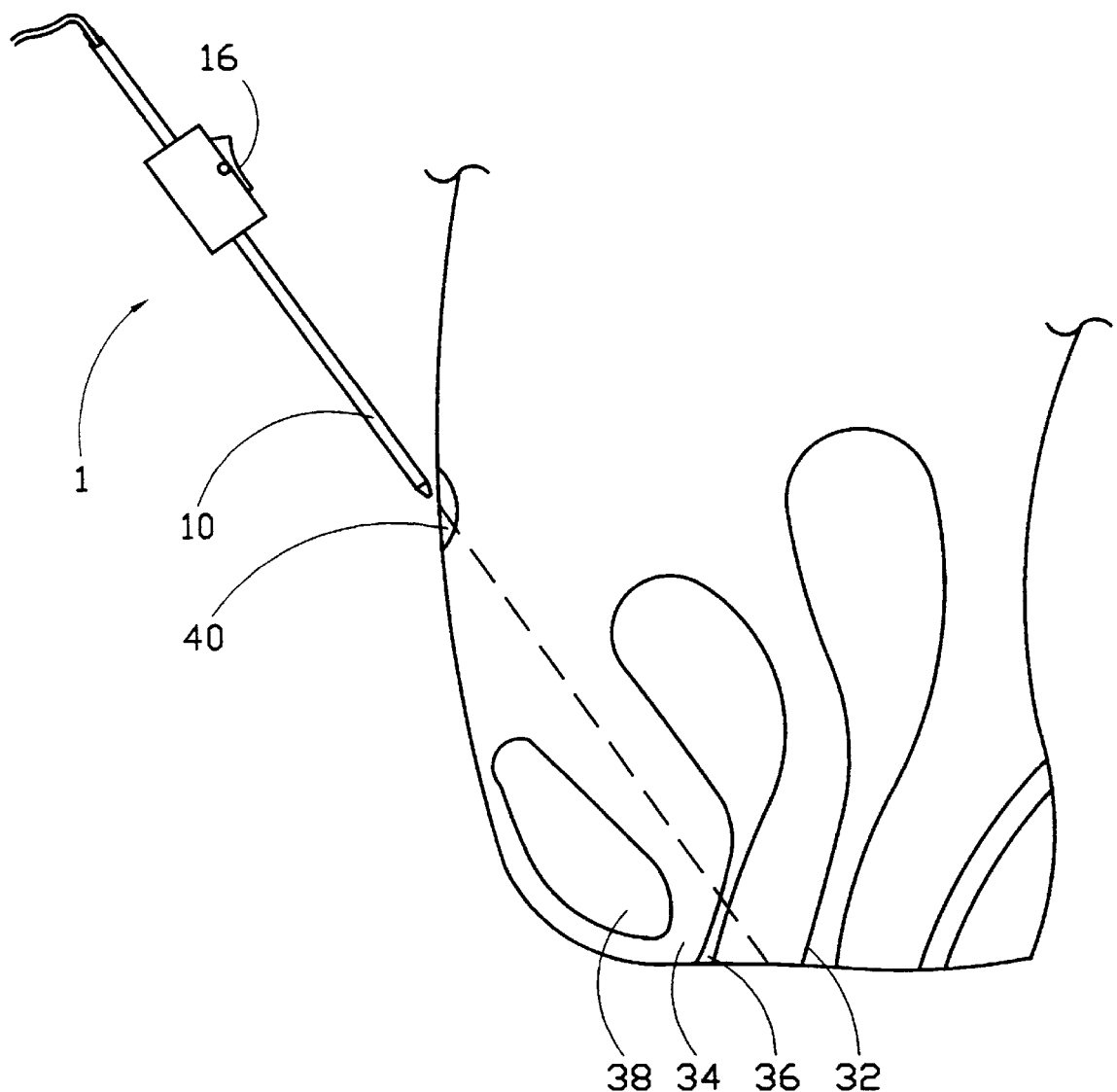
FIG. 4 is a cross sectional view of a female pubic area and placement of an incontinence needle before insertion through the abdomen in accordance with the present invention.

The incontinence needle 1 is used in the following manner. With reference to FIG. 4, an incision 40 is made in the abdomen. The center of the incision 40 is preferably 2–3 inches above the pubic bone 38. The incision 40 is preferably vertical and 3 inches long. The depth of the incision 40 is preferably 2–4 inches. The depth of the incision 40 is dependent upon the thickness of the fat layer, the thicker the fat layer, the deeper the incision.

Figure 5:
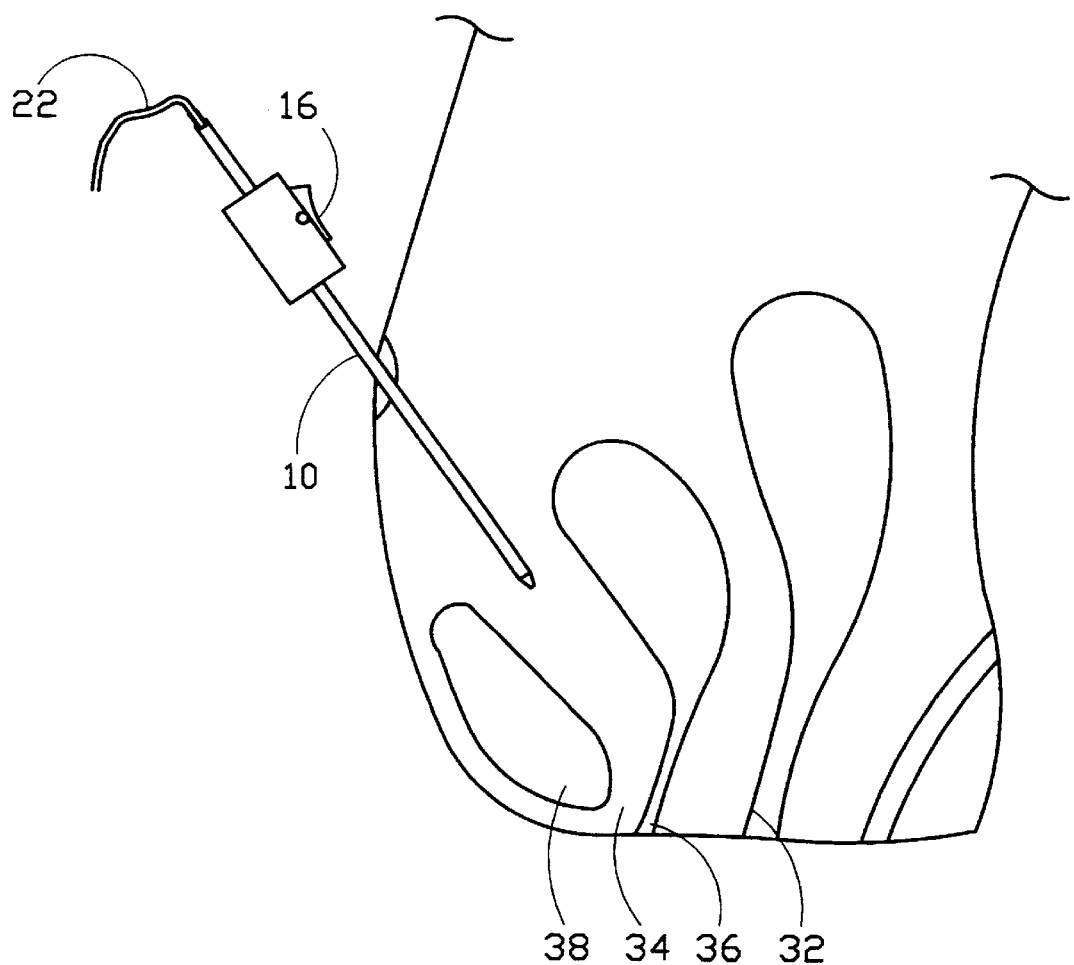
FIG. 5 is a cross sectional view of a female pubic area and insertion of an incontinence needle through the abdomen and behind the pubic bone in accordance with the present invention.

The needle 10 is inserted into the incision 40. The finger grip 12 is locked at a comfortable position along the length of the needle 10. A forefinger and thumb of one hand is used to guide the needle 10 through the tissue and the forefinger and thumb of the other hand is used to drive the needle 10 with the finger grip 12. The needle 10 travels through tissue in the abdomen and behind the pubic bone 38. With reference to FIG. 5, as the needle 10 travels through the tissue, the finger grip 12 may be unlocked, slid back and then relocked with the driving forefinger and thumb. The surgeon must be careful not to pierce or nick the urethra 36, but to go to the left or right side of the urethra 36 when driving the needle 10 through the tissue 34. The guiding forefinger is used to help direct the needle 10 to the left or right of the urethra and to ensure that the needle exits above the vagina 32.

Figure 6:
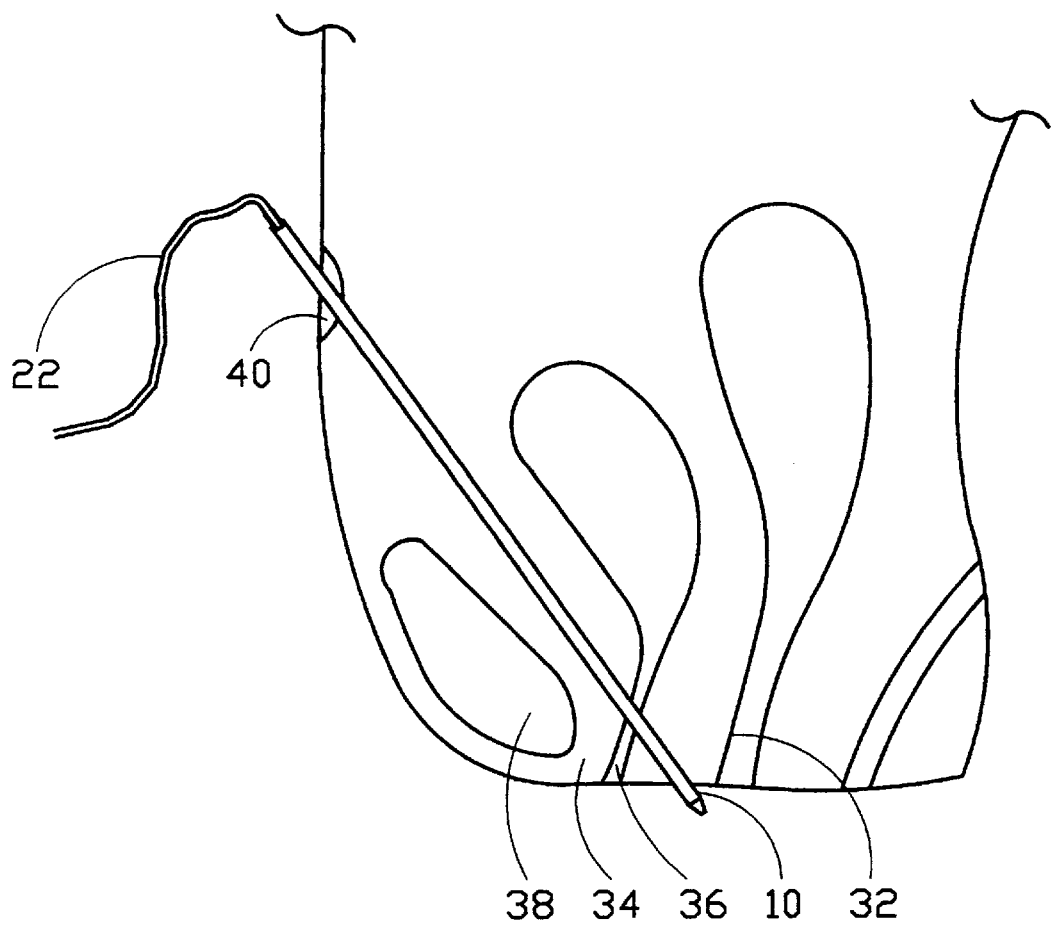
FIG. 6 is a cross sectional view of a female pubic area and a fully inserted needle in accordance with the present invention.

With reference to FIG. 6, when a sufficient length of needle protrudes from the tissue above the vagina 32, the finger grip 12 is removed. The needle 10 is pulled all the way through and the suture 22 is cutoff the end of the needle 10. The ends of the suture 22 are tied or fastened together such that pressure is applied to help keep the urethra 36 closed. Two sutures 22 are required, one on the left side of the urethra 36 and the other on the right side of the urethra 36.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. An incontinence needle comprising:
    a needle having a blunt tip on one end and a suture swaged on the other end thereof;
    a finger grip having a rocker arm which is pivotally connected to a slidable base with a pivot pin, a bottom of said rocker arm having a cam surface, wherein when said rocker arm is in a first position, said cam surface preventing movement of said finger grip relative to said needle, when said rocker arm is in a second position, said cam surface allowing said finger grip to be slidable to said needle.
2. The incontinence needle of claim 1, wherein:
    a top surface of said rocker arm having a non-slip surface.
3. The incontinence needle of claim 1, wherein:
    said slidable base having a bore through a length thereof, said bore being sized to slidably receive said needle.
4. The incontinence needle of claim 1, wherein:
    said slidable base having a cavity disposed in a top thereof to provide clearance for said rocker arm to toggle between a first and second position.
5. The incontinence needle of claim 1, wherein:
    a cutout being formed in a bottom of said slidable base.
6. The incontinence needle of claim 1, wherein:
    said needle having a cross-sectional shape which is round.
7. The incontinence needle of claim 1, wherein:
    said needle having a cross-sectional shape which is oval.
8. The incontinence needle of claim 1, wherein:
    said needle being flexible.
9. An incontinence needle comprising:
    a needle having a blunt tip on one end and a suture swaged on the other end thereof;
    a finger grip having a rocker arm which is pivotally connected to a slidable base with a pivot pin, said slidable base having a bore through a length thereof, said bore being sized to slidably receive said needle, a bottom of said rocker arm having a cam surface, wherein when said rocker arm is in a first position, said cam surface preventing movement of said finger grip relative to said needle, when said rocker arm is in a second position, said cam surface allowing said finger grip to be slidable to said needle.

10. The incontinence needle of claim 9, wherein:

a top surface of said rocker arm having a non-slip surface.

11. The incontinence needle of claim 9, wherein:

said slidable block having a cavity disposed in a top thereof to provide clearance for said rocker arm to toggle between a first and second position.

12. The incontinence needle of claim 9, wherein:

a cutout being formed in a bottom of said slidable base.

13. The incontinence needle of claim 9, wherein:

said needle having a cross-sectional shape which is round.

14. The incontinence needle of claim 9, wherein:

said needle having a cross-sectional shape which is oval.

15. The incontinence needle of claim 9, wherein:

said needle being flexible.

16. A method for performing a procedure which relieves urinary incontinence, comprising the steps of:

making an incision in the abdomen above the pubic bone driving a needle with a blunt tip through the incision and behind the public bone;

guiding said needle around the urethra and above the vagina with a forefinger;

cutting a suture off an end of said needle; and fastening ends of said suture such that pressure is applied to help close the urethra.

17. The method for performing a procedure which relieves urinary incontinence of claim 16 further comprising:

said needle having a finger grip which may be used to drive said needle in a first position, said finger grip being slidable relative to said needle in a second position.

* * * * *